United States Patent [19]

Klemann et al.

[11] Patent Number: 5,043,179

[45] Date of Patent: Aug. 27, 1991

[54] TRIOL TRIESTER DERIVATIVES AS LOW CALORIE FAT MIMETICS

[75] Inventors: Lawrence P. Klemann, Somerville; John W. Finley, Whippany; Anthony Scimone, Cedar Grove; Edward L. Wheeler, Fairfield; Ronald G. Yarger, Convent Station; Joseph Lupia, Lake Hiawatha, all of N.J.

[73] Assignee: Nabisco Brands, Inc., Parsippany, N.J.

[21] Appl. No.: 501,027

[22] Filed: Mar. 29, 1990

[51] Int. Cl.$^5$ .................. A23D 7/00; C07C 69/66
[52] U.S. Cl. .................. 426/531; 426/566; 426/601; 426/611; 426/804; 560/125
[58] Field of Search ............ 426/611, 601, 804, 566, 426/531; 560/185

[56] References Cited

U.S. PATENT DOCUMENTS

| | | | |
|---|---|---|---|
| 519,980 | 5/1894 | Winter . | |
| 2,924,528 | 2/1960 | Bursky et al. | 99/118 |
| 2,993,063 | 7/1961 | Alsop et al. | 260/410.6 |
| 3,495,010 | 2/1970 | Fossel | 424/312 |
| 3,579,548 | 5/1971 | Whyte | 260/410.7 |
| 3,600,186 | 8/1971 | Mattson et al. | 99/1 |
| 3,637,774 | 1/1972 | Babayan et al. | 260/410.6 |
| 3,876,794 | 4/1975 | Rennhard | 426/152 |
| 4,005,195 | 1/1977 | Jandacek | 657/528 |
| 4,304,768 | 12/1981 | Staub et al. | 424/180 |
| 4,508,746 | 4/1985 | Hamm | 506/234 |
| 4,582,715 | 4/1986 | Volpenhein | 426/601 |
| 4,631,196 | 12/1986 | Zeller | 426/580 |
| 4,797,300 | 1/1989 | Jandacek et al. | 426/549 |
| 4,830,787 | 5/1989 | Klemann et al. | 260/410 |
| 4,849,242 | 7/1989 | Kershner | 426/601 |
| 4,861,613 | 8/1989 | White et al. | 426/611 |

FOREIGN PATENT DOCUMENTS

| | | |
|---|---|---|
| 1106681 | 11/1978 | Canada . |
| 205273 | 5/1986 | European Pat. Off. . |
| 233856 | 2/1987 | European Pat. Off. . |
| 3529564 | 8/1987 | Fed. Rep. of Germany . |
| 207070 | 2/1984 | German Democratic Rep. . |

OTHER PUBLICATIONS

Brockerhoff H., Biochim. Biophys. Acta 212: 92-101 (1970).
Mattson, F. H., and Volpenhein, R. A. J. Lipid Res. 10:217-276 (1969).
Altshul, A. M., Scientific Status Summary, Institute of Food Technologists, April (1989), pp. 1 to 12.
Booth, A. M. and Gros, A. T., 40 J. Amer. Oil Chem. Soc. 551-553 (1963).
Goodman, and Gilman's Pharmacological Basics of Therapeutics, 7th ed., MacMillian Pub., N.Y. 1002-1003 (1985).
Gottenbos, J. J., Chapter 8, Beare-Rogers, J. ed., A. O. C. S., pp. 107-112 (1988).
Halliburton, W. D. et al., 13 J. Biol. Chem. 296-301 (1919).
Hamm, D. J. 49 J. Food Sci. 419-428 (1984).
Haumann, B. J., 63 J. Amer. Oil Chem. Soc 278-287 (1986).
La Barge, R. G., 42 Food Tech. 84-88 (1988).
Lapworth, A. and Pearson, L. K., 13 J. Biol. Chem. 296-300 (1919).
Markley, K. S., 2nd ed., Part II, Krieger Pub. Co. 785-787, 797-811 and 817-820 (1983).
Mattson, F. H., and Nolen, G. A., 102 J. Nurti, 1171-1175 (1972).
Mattson, F. H. and Volpenhein R. A., 13 J. Lipids Res. 325-328 (1972).
Mattson, F. H. and Volpenhein, R. A., 13 J. Lipids Res. 777-782 (1972).
Mattson, F. H., and Volpenhein, R. A., 102 J. Nutri. 1177-1180 (1972).
Merten, H. L., 18 Agr. Food Chem. 1002-1004 (1970).
Neissner, R., 80 Fette, Seifen, Anstrichmittel 303-311 (1978), Abstract Only.
Neissner, R., 80 Fette, Seifen, Anstrichmittel 461-464 (1978), Abstract Only.
Stryker, W. A., 31 Arch. Path 670-692 (1941).

Primary Examiner—Donald E. Czaja
Assistant Examiner—Evan Federman

[57] ABSTRACT

Triol triester derivatives, notably compounds having a four- to thirty- carbon backbone to which are attached three fatty $C_1$ or $C_2$ to $C_{29}$ ester groups in ester linkage are edible, preferably partially digestible, fat replacements for foods and pharmaceuticals.

23 Claims, No Drawings

TRIOL TRIESTER DERIVATIVES AS LOW CALORIE FAT MIMETICS

BACKGROUND OF THE INVENTION

This invention relates to the use of triol triester derivatives as edible synthetic fat replacements in food and pharmaceuticals. These compounds have a four- to thirty- carbon backbone to which are attached three fatty $C_1$ or $C_2$ to $C_{29}$ aliphatic, ether, or ester groups in ester linkage. Preferred compounds are partially digestible.

Reduction in caloric intake can be significantly enhanced by dietary fat reduction, since fats provide nine calories per gram compared to four calories per gram provided by protein or carbohydrates. Furthermore, dietary fats represent a large percentage (approximately 40) of the daily caloric intake (Merten, H. L., 18 *J. Agr. Food Chem.* 1002 (1970)). Not only are fats high in calories, but certain fats appear to pose a health risk when consumed in large quantities over time. In 1988, the Surgeon General issued a report, "Nutrition and Health, " which summarized available scientific evidence for the role of diet in health promotion and disease prevention, and comprehensively documented the basis for recommended dietary changes. A main conclusion of this report was that overconsumption of certain dietary components is now a major concern for Americans, who disproportionately consume foods high in fat, often at the expense of foods high in complex carbohydrates and fiber that may be more conducive to health (Altschul, A. M., "Low Calorie Foods " Scientific Status Summary, Institute of Food Technologists, April 1989). A number of other national advisory committees on nutrition have made recommendations differing in detail, but the common theme is a reduction in the total amount of fat in the diet (Gottenbos, J. J., chapter 8 in Beare-Rogers, J., ed., *Dietary Fat Requirements in Health and Development*, A.O.C.S. 1988, page 109). Hence, major research efforts have focused on ways to produce food substances that provide the same functional and organoleptic properties as fats, but not the calories.

A major strategy for developing low calorie replacement fats has been to structurally re-engineer natural triglycerides in such a way as to retain their conventional functional properties in foods, while removing their susceptibility toward hydrolysis or subsequent absorption during digestion. To this end, the fatty acids attached to glycerol have been replaced with alternate acids (U.S. Pat. No. 3,579,548 to Whyte and U.S. Pat. No. 4,582,715 to Volpenhein); groups have been inserted between the fatty acids and the glycerol backbone ("propoxylated glycerols", U.S. Pat. No. 4,861,613 to White and Pollard); the ester linkages have been replaced by ether linkages (Can. Pat. No. 1,106,681 to Trost); the ester linkages have been reversed (U.S. Pat. No. 4,508,746 to Hamm); and the glycerol moeity has been replaced with an alternate alcohol (e.g., ethylene glycol in U.S. Pat. No. 2,924,528 to Barskey et al., and U.S. Pat. No. 2,993,063 to Alsop and Carr).

A second major approach to the development of a low calorie fat replacement has been to explore or synthesize non-absorbable polymeric materials structurally unlike triglycerides, but having physical properties similar to edible fat. Mineral oil was disclosed as early as 1894 (U.S. Pat. No. 519,980 to Winter), and, more recently, polydextrose (U.S. Pat. No. 4,631,196 to Zeller), polyglucose and polymaltose (U.S. Pat. No. 3,876,794 to Rennhard), polysiloxane (Eur. Pat. Ap. No. 205,273 to Frye), jojoba wax (W. Ger. Pat. No. 3,529,564 to Anika), and polyethylene polymers (E. Ger. Pat. No. 207,070 to Mieth, et al.) have been suggested.

A third major strategy combines the first two. Rather than restructure triglyceride molecules or find substitutes structurally very dissimilar, this approach explores the use of various polyol esters, compounds which have numbers of fatty acid groups in excess of the three in conventional fat triglycerides, as nonabsorbable fat replacements. Fully esterified sugar alcohols were suggested as fat replacements during World War I (notably mannitol, Lapworth, A., and Pearson, L. K., and Halliburton, W. D., et al., 13 *J. Biol. Chem.* 296 and 301 (1919)); Minich suggested esterifying pentaerythritol, a tetrahydric neopentyl sugar alcohol which can be formed from pentaerythrose, in 1960; and the Southern and Western Regional Research Laboratories of the U.S.D.A. investigated the feasibility of using amylose esters as new-type fats during the 1960's (see Booth, A. N., and Gros, A. T., 40 *J. Amer. Oil Chem. Soc.* 551 (1963) and the references cited therein). The same U.S.D.A. group further determined the caloric availability and digestibility of a series of dimeric and polymeric glycerides including diglyceride esters of succinic, fumaric, and adipic acids, and polymeric fats from stearic, oleic and short-chain dibasic acids for possible use as low calorie fats. Polyglycerol esters were suggested in 1972 (U.S. Pat. No. 3,637,774 to Babayan and Lehman).

Also in 1972, a series of papers was published which described studies assessing a series of compounds having from one to eight hydroxyl groups esterified with fatty acids. In vitro, purified pancreatic lipase did not hydrolyze polyols having more than three hydroxyl groups esterified (Mattson, F. H., and Volpenhein, R. A., 13 *J. Lipid Res.* 325 (1972), summarized in Table 1, page 327). However, a crude preparation of bile and pancreatic fluid hydrolyzed, to some extent, all substrates having from one to five ester groups esterified. Substrates having 6 to 8 hydroxyl groups esterified were not cleaved (ibid.). The investigators attributed the hydrolysis of substrates having four or five esterified groups to a "nonspecific lipase " that could be deactivated by the addition of a proteolytic enzyme, alpha-chymotrypsin (ibid, column 2, paragraph 2).

The "nonspecific lipase " also appeared to hydrolyze methyl oleate, ethylene glycol dioleate and glycerol trioleate in an enzyme preparation containing pancreatic lipase inhibited by taurocholate (see ibid., Table 1, and page 328, column 1, last paragraph, ending the article at column 2). A subsequent paper confirmed the stepwise hydrolysis of erythritol tetraoleate by "nonspecific lipase " (Mattson, F. H., and Volpenhein, R. A.,13 *J. Lipid Res.* 777 (1972)).

The same research group then fed a series of polyol fatty acid esters to rats (Mattson, F. H., and Nolen, G. A., 102 *J. Nutr.* 1171 (1972)). In a fat balance study, compounds having less than four hydroxyl groups esterified (specifically, methyl oleate, ethylene glycol oleate, and glycerol trioleate) were absorbed (Table 4, page 1174). As the number of ester groups increased (erythritol and pentaerythritol tetraoleate and xylitol pentaoleate), the absorbability decreased; sorbitol hexaoleate and sucrose octaoleate were not absorbed (ibid.). The investigators concluded that absorbability decreased by increasing the number of esterified hydroxyl groups (Discussion, page 1174, column 1 through page 1175, column 2).

The research was continued with a tracer study comparing the rates of absorption of fatty acids of fully esterified glycerol, erythritol, xylitol and sucrose as measured in thoracic duct cannulated rats (see Mattson, F. H., and Volpenhein, R. A., 102 *J. Nutr.* 1177 (1972)). Fatty acids fed as the erythritol tetraester appeared in the lymph at a slower rate than glycerol trioleate, but achieved the same level after 12 hours (see page 1179, column 1, lines 2-6 and column 2, FIGS. 2 and 3). Finding free tagged erythritol in the urine, the investigators concluded the tetraester was hydrolyzed in vivo (column 1, line 2 from to the bottom to column 2, line 8).

As a result of these studies, the investigators concluded that the number of hydroxyl groups esterified to be important indicia of digestibility, and patented the use of polyols, notably sucrose, having at least 4 hydroxyl groups esterified per molecule as low calorie fat replacements (see U.S. Pat. No. 3,600,186 to Mattson and Volpenhein and others following, such as, for example, U.S. Pat. No. 4,797,300 to Jandacek).

Nondigestible or nonabsorbable triglyceride analogues, polymeric materials, and polyol esters have proved disappointing as fat replacements when tested in feeding trials, where gastrointestinal side effects occurred, in some cases so extreme that frank anal leakage was observed (for recent reviews, see Hamm, D. J., 49 *J. Food Sci.* 419 (1984), Haumann, B. J., 63 *J. Amer. Oil Chem. Soc.* 278 (1986), and LaBarge, R. G., 42 *Food Tech.* 84 (1988)). Nondigestible fats act as a laxative and are expelled from the body, eliciting foreign body reactions like those early documented for mineral oil (Stryker, W. A., 31 *Arch. Path.* 670 (1941), more recently summarized in Goodman and Gilman's *Pharmacological Basis of Therapeutics*, 7th ed., Macmillan Pub. Co., N.Y. 1985, pp. 1002-1003). Polyglycerol and polyglycerol esters, for example, suggested as fat replacements supra, have been suggested for use as fecal softening agents as well (U.S. Pat. No. 3,495,010 to Fossel). A number of remedies have been recommended to combat the anal leakage observed when sucrose polyesters are ingested (e.g., employing cocoa butters, U.S. Pat. No. 4,005,195 to Jandacek, or incorporating saturated fatty groups, Eur. Pat. Ap. No. 233,856 to Bernhardt), and dietary fiber preparations have been incorporated into polysaccharide and/or polyol-containing foodstuffs to help inhibit the diarrheal effect (U.S. Pat. No. 4,304,768 to Staub et al.).

Subsequently, carboxy/carboxylates were suggested as edible, preferably partially digestible, fat mimetics (U.S. Pat. No. 4,830,787 to Klemann and Finley). These compounds have at least three aliphatic groups attached to a two- to five-carbon backbone with at least one conventional ester bond (forming a carboxy and/or methyl carboxy functionality) and at least one reversed ester bond (forming a carboxylate or methyl carboxylate functionality) as compared to conventional triglycerides. Preferred compounds were partially digestible, simultaneously achieving reduced caloric value while reducing problems associated with non-metabolizable fat substitutes. Polyoxyalkylene fatty acid esters have also been recently suggested as non-laxative fat replacements (U.S. Pat. No. 4,849,242 to Kershner).

SUMMARY OF THE INVENTION

An object of the present invention is to provide a new group of fat replacement compounds. More particularly, it is an object of a preferred embodiment of the present invention to provide a partially digestible fat replacement which avoids diarrhea and other laxative side effects. It is a further object of a preferred embodiment of the present invention to provide a partially digestible fat replacement which may, if desired, be engineered to provide essential or desirable fatty acids.

These and other objects are accomplished by the present invention, which describes a new class of edible synthetic fat replacements for food use: triol triesters, methods of using them, and food compositions incorporating them. Triol triesters are structurally analogous to natural triglycerides in that both have three fatty groups attached in conventional ester linkage to aliphatic backbones, but triol triesters have different backbones than triglycerides. Triol triesters may be described by the following structural formula

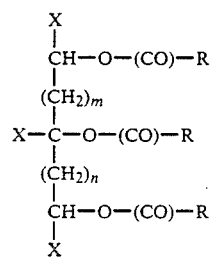

where $m = 0$ to 20, $n = 0$ to 20, $X = H$ or an aliphatic having 1 to 20 carbons, the X groups being the same or different, and each R is, independently, a $C_1$ to $C_{29}$ aliphatic group, a $C_2$ to $C_{29}$ ether group of the formula $R'-O-R''-$, or a $C_2$ to $C_{29}$ ester group of the formula $$R''-O-(CO)-R'- \text{ or } R'-(CO)-O-R''-,$$

where $R'-$ and $R''-$ are, independently, aliphatic groups, subject to the proviso that, when $X = H$, then $m + n \geq 1$ and to the proviso that the number of carbons in the X groups, together with the sum of $m + n$, does not exceed 25.

DETAILED DESCRIPTION OF THE INVENTION

The present invention is based on the finding that appropriate structural combinations of three fatty acids or fatty acid derivatives esterified to hydrocarbon backbones have the property of limited caloric availability. Preferred structures are partially digestible.

This invention describes a new class of edible synthetic fat mimetic compounds. The compounds, called triol triesters or triol triester derivatives, can be defined by the following structural formula:

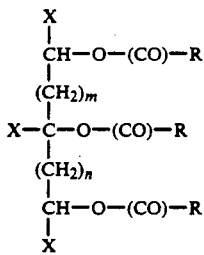

where
m=0 to 20,
n=0 to 20,
X=H or an aliphatic having 1 to 20 carbons, the X groups being the same or different, and
each R is, independently, a $C_1$ to $C_{29}$ aliphatic group, a $C_2$ to $C_{29}$ ether group of the formula R'—O—R"—, or a $C_2$ to $C_{29}$ ester group of the formula R"—O—(CO)—R'— or R'—(CO)—O—R"—, where R'— and R"— are, independently, aliphatic groups, subject to the proviso that, when X=H, then $m+n \geq 1$ and to the proviso that the number of carbons in the X groups, together with the sum of m +n, does not exceed 25.

The triol triesters of this invention encompass compounds having the following formula

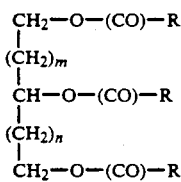

where
m=1 to 14,
n=0 to 14,
provided that $m+n \leq 26$, and
R is as defined above.

The triesters of this invention further encompass compounds of the formula

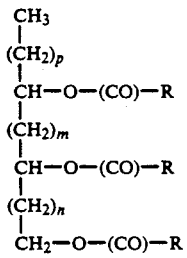

where
m=0 to 13,
n=0 to 13,
p=0 to 13,
provided that $m+n+p \leq 26$, and
R is as defined above.

The compounds of this invention comprise $C_4$ to $C_{30}$ aliphatic triols esterified with fatty acids or fatty acid derivatives. The triols may be linear or branched, saturated or unsaturated. Example triols include butanetriol, pentanetriol, hexanetriol, heptanetriol, octanetriol, nonanetriol, decanetriol, undecanetriol, dodecanetriol, and so forth. As used herein, chemical names and formulae include isomeric variations.

The fatty groups R may be the same or different, and may comprise a mixture of substituents The R groups may be aliphatic groups, ether groups of the formula R'—O—R"—, or ester groups of the formula R"—O—(CO)—R'— or R'—(CO)—O—R"—, where R'— and R"— are aliphatic groups, provided that the sum of the number of carbon atoms in R' and R" be 2 to 29. R, R', and R" may be saturated or unsaturated, with linear or branched chains. By an "aliphatic " group is meant a monovalent radical derived from an aliphatic hydrocarbon by the removal of a hydrogen.

Fatty groups R may be derived from fatty acids. The term "fatty acid " used here means an organic fatty acid of the formula RCOOH containing 2 to 30 carbons, and may be synthetic or natural, saturated or unsaturated, with straight or branched chains. Examples of fatty acids are acetic, propionic, butyric, caproic, caprylic, pelargonic, capric, undecanoic, lauric, myristic, palmitic, margaric, stearic, arachidic, behenic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, docosahexaenoic, and the like acids. Mixtures of fatty acids may also be used, such as that obtained from non-hydrogenated, partially hydrogenated or fully hydrogenated soybean, safflower, sunflower, sesame, peanut, corn, olive, rice bran, canola, babassu nut, coconut, palm, palm kernel, lupin, nasturtium seed, mustard seed, cottonseed, low erucic rapeseed, butter or marine oils, or plant waxes such as jojoba. Specific fractions of natural or processed oils or waxes may also be used.

R may also be an ester derivative of the formula R"—O—(CO)—R'— or R'—(CO)—O—R"—, with the ester bond in either direction. Thus, R may be a dicarboxylate-extended fatty group. By "dicarboxylate-extended " fatty group is meant a group formed from the reaction of fatty alcohols with dicarboxylic acids, such as, for example, malonic, succinic, glutaric or adipic acid. The resulting malonyl, succinyl, glutaryl or adipoyl-extended fatty R groups are, structurally, aliphatic alcohols with their chains extended by the radicals —OC—CH$_2$—CO— (malonyl), —OC—(CH$_2$)$_2$—CO— (succinyl), —OC—(CH$_2$)$_3$—CO—(glutaryl), —OC—(CH$_2$)$_4$—CO—(adipoyl), and the like. Thus, if a fatty alcohol is denoted by R"OH, a malonyl-extended fatty ester group R would be R"—O—(CO)—CH$_2$—, a succinyl-extended fatty ester group R would be R"—O—(CO)—(CH$_2$)$_2$—, a glutaryl-extended fatty group would be R"—O—(CO)—(CH$_2$)$_3$— and so forth. Formulae used herein include isomeric variations.

R may also be an ester derivative that is an hydroxycarboxylic acid-extended fatty group, with the ester bond reversed as compared to dicarboxylate-extended groups. By an "hydroxycarboxylic acid-extended fatty group " is meant a group formed from the reaction between a fatty acid and the hydroxyl group of a hydroxycarboxylic acid, such as, for example, one in the lactic acid series such as glycolic (hydroxyacetic, CH$_2$OH—COOH), hydracrylic (3-hydroxypropanoic acid, CH$_2$OH—CH$_2$—COOH), hydroxybutanoic acid (4-hydroxybutanoic, CH$_2$OH—(CH$_2$)$_2$—COOH, or the 2— or 3— isomer), hydroxypentanoic acid (5-hydroxypentanoic, CH$_2$OH—(CH$_2$)$_3$—COOH, or the 2—, 3—, or 4—isomer), and so forth. Thus, if a fatty acid is denoted by R'COOH, a glycolic-extended fatty group R would be denoted R'—(CO)—O—CH$_2$—, a hydracrylic-extended fatty group R would be denoted R'—(CO)—O—(CH$_2$)$_2$—, and so forth. Ester side chains of this type may also be derived from hydroxy fatty acids (e.g., ricinoleic or hydroxystearic acids) having an acylated hydroxyl group. An acetyl ricinoleoyl R group would, for example, have the formula —(CH$_2$)$_7$—CH=CHCH$_2$—CH(O(CO)CH$_3$)—(CH$_2$)$_5$CH$_3$.

R may also be an ether group having 2 to 30 carbon atoms of the formula R'—O—R"—, with R' and R" as defined above, that is, an oxaalkyl chain having an ether group (—O—) anywhere in the chain. This type of R group may be derived from etheric carboxylic acids.

The R groups will be selected to provide a discernible fatty character in the compounds. Thus, most of the R groups have 3 or more carbon atoms, with a percentage containing 3 to 23 (derived from acids having 4 to 24 carbons), more narrowly 9 to 19, and even more narrowly 15 to 17 carbon atoms (derived from acids having 16 to 18 carbons). Preferred triol triesters can have an array of R groups selected to include 95% having 13 to 17 carbon atoms (derived from acids having 14 to 18 carbons). In one embodiment, the R groups should predominantly be in the range of 13 to 17 carbon atoms and be saturated. In another embodiment, the R groups should be predominantly in the range of 15 to 17 carbon atoms and be unsaturated (with a preponderance of monounsaturated groups).

The choice, number and arrangement of R groups will affect the biological as well as physical properties of the compounds. Where, by virtue of any of these factors, the R groups are metabolized, the caloric value of the compound will increase. Among the preferred compounds are those which are partially digestible and contribute 0.5 to 8.5 kcal/gram, more narrowly 2.0 to 8.0 kcal/gram, even more narrowly 1.0 to 6.0 kcal/gram upon being metabolized. For some applications, compounds having approximately a third or less of the calories of natural triglyceride fat are particularly desirable. For other applications, compounds having about one half to two-thirds the calories are desirable.

Thus, in the preferred class of compounds, the R groups exhibit differential reactivity on digestion. This results not only in the controlled and limited availability of effective caloric value, but also the selective conversion of the fat mimetic to a product or intermediate with a less oil-like nature. The more readily digestible aliphatic residue can be a highly desirable essential acid or a nutritionally advantageous carboxylic acid such as oleic, linoleic, linolenic, or eicosapentaenoic acids, as well as low molecular weight carboxylic acids (e.g., acetic, propionic, or butyric acids) which would limit caloric delivery and provide additional ability to control functionality.

As with natural triglycerides, the more readily digestible residue can, alternatively, be a fatty acid having beneficial attributes, such as, for example, those associated with conjugated linoleic acid isomers. The product of such a controlled digestive process may be said to have decreased hydrophobicity, and correspondingly increased hydrophilicity, relative to its fat mimetic precursor. Such a product of a process of controlled digestion would tend to have not only decreased oiliness, but also increased ability to function as an emulsifier. Such a controlled digestion product will be less prone to exist in the GI tract as a persistent oil compared with substances taught in the prior art. Ideally, the enhanced emulsifying capacity of the enzymatic cleavage product derived from compositions of the invention would actually be an aid to digestion, substantially overcoming a major problem which has heretofore limited the widespread use and development of highly desirable low calorie synthetic fats and oils in foods and food preparation.

The triol triesters of this invention may be incorporated either alone, or in combination with another fat and/or fat mimetic, into any food composition or used in conjunction with any edible material. Other fat mimetics include any heretofore suggested edible fat replacements, including, but not limited to, sugar esters, neoalkyl esters, polyglycerol esters, malonate esters, propoxylated glycerols, retrofats, silicone oils/siloxanes, carboxy/carboxylates, and the like. The term "edible material" is broad and includes anything edible whether or not intended for nutrition, i.e., it can be an additive such as an antioxidant for fats or oils, an antispatter agent, an emulsifier, a texture modifier such as a plasticizer for chewing gum, a cosmetic or coating component, or other minor functional ingredient such as a carrier or diluent for use in flavorings, pharmaceuticals, and the like. Representative of edible materials which can contain the fat mimetic compounds of this invention in full or partial replacement of natural fat are: frozen desserts, e.g., ice cream, frozen novelties, milk shakes or sherbert; puddings and pie fillings; margarine substitutes or blends; flavored bread or biscuit spreads; mayonnaise; salad dressings; filled dairy products such as filled cream or filled milk; dairy or non-dairy cheese spreads; coffee lighteners, liquid and dried; flavored dips; frying fats and oils; reformed and comminuted meats; pet foods; meat substitutes or extenders; whipped toppings; compound coatings; frostings, fillings, and icings; cocoa butter replacements or blends; candy, especially fatty candies such as those containing peanut butter or chocolate; chewing gum, bakery products, e.g., cakes, breads, rolls, pastries, cookies, biscuits, and savory crackers; mixes or ingredient premixes for any of these; breakfast cereals; as well as flavor, nutrient, drug or functional additive delivery systems.

The following is a list of representative, but not limiting, examples of specific triol triester derivatives of this invention:

1,2,4-Butane Trioleate

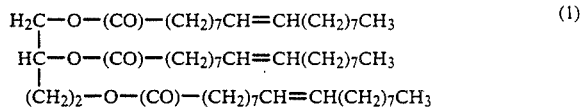

(1)

1,3,5-Pentane Trioleate

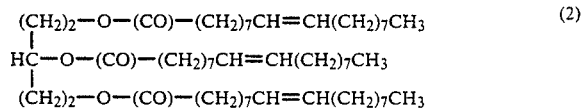

(2)

1,2,6-Hexane Trioleate

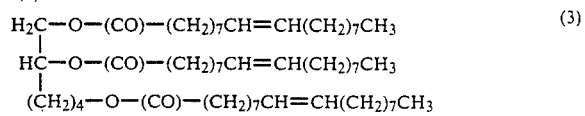

(3)

1,2,3-Heptane Tri-10-undecenoate

-continued (4)
$$H_2C-O-(CO)-(CH_2)_8CH=CH_2$$
$$(HC-O-(CO)-(CH_2)_8CH=CH_2)_2$$
$$(CH_2)_3CH_3$$

1,2,8-Octane Tri-10-undecenoate (5)
$$H_2C-O-(CO)-(CH_2)_8CH=CH_2$$
$$HC-O-(CO)-(CH_2)_8CH=CH_2$$
$$(CH_2)_6-O-(CO)-(CH_2)_8CH=CH_2$$

1,2,3-Dodecane Trioleate (6)
$$(CH_2)_8CH_3$$
$$HC-O-(CO)-(CH_2)_7CH=CH(CH_2)_7CH_3$$
$$HC-O-(CO)-(CH_2)_7CH=CH(CH_2)_7CH_3$$
$$H_2C-O-(CO)-(CH_2)_7CH=CH(CH_2)_7CH_3$$

Pentane 1,5-Dioleate-3-Palmitate (7)
$$H_2C-O-(CO)-(CH_2)_7CH=CH(CH_2)_7CH_3$$
$$CH_2$$
$$HC-O-(CO)-(CH_2)_{14}CH_3$$
$$CH_2$$
$$H_2C-O-(CO)-(CH_2)_7CH=CH(CH_2)_7CH_3$$

Dec-6-ene 2,3-Di(oleyloxysuccinate)-1-Oleate (8)
$$(CH_2)_2CH=CH(CH_2)_2CH_3$$
$$HC-O-(CO)-(CH_2)_2-(CO)-O-(CH_2)_8CH=CH(CH_2)_7CH_3$$
$$HC-O-(CO)-(CH_2)_2-(CO)-O-(CH_2)_8CH=CH(CH_2)_7CH_3$$
$$H_2C-O-(CO)-(CH_2)_7CH=CH(CH_2)_7CH_3$$

Pentane 1-Oleate-3-(3-Palmityloxypropionate)-5-Myristate (9)
$$(CH_2)_2-O-(CO)-(CH_2)_7CH=CH(CH_2)_7CH_3$$
$$HC-O-(CO)-CH_2CH_2-O-(CH_2)_{16}CH_3$$
$$(CH_2)_2-O-(CO)-(CH_2)_{12}CH_3$$

6-Methylheptane-3-(9-Ethoxypelargonate)-1,4-Dipalmitate

(10)
$$(CH_2)_2-O-(CO)-(CH_2)_{16}CH_3$$
$$HC-O-(CO)-(CH_2)_8-O-CH_2-CH_3$$
$$HC-O-(CO)-(CH_2)_{16}CH_3$$
$$CH_2-CH(CH_3)_2$$

Decane 1-Laurate-2,10-Di(pelargonyloxysuccinate)

(11)
$$H_2C-O-(CO)-(CH_2)_{10}CH_3$$
$$HC-O-(CO)-(CH_2)_2-(CO)-O-(CH_2)_8CH_3$$
$$H_2C-(CH_2)_7-O-(CO)-(CH_2)_2-(CO)-O-(CH_2)_8CH_3$$

1,2,6-Hexane Tri-10-undecenoate

(12)
$$H_2C-O-(CO)-(CH_2)_8CH=CH_2$$
$$HC-O-(CO)-(CH_2)_8CH=CH_2$$
$$(CH_2)_4-O-(CO)-(CH_2)_8CH=CH_2$$

1,2,6-Hexane Trimyristate

(13)
$$H_2C-O-(CO)-(CH_2)_{12}CH_3$$
$$HC-O-(CO)-(CH_2)_{12}CH_3$$
$$(CH_2)_4-O-(CO)-(CH_2)_{12}CH_3$$

1,2,4-Butane Triester

-continued

(14)
$$H_2C-O-(CO)-R_1$$
$$HC-O-(CO)-R_2$$
$$(CH_2)_2-O-(CO)-R_3$$

where $R_1$, $R_2$, and $R_3$ are a mixture comprising $-C_{13}H_{27}$, $-C_{15}H_{31}$, and $-C_{17}H_{33}$ groups 1,3,5-Pentane Triester

(15)
$$(CH_2)_2-O-(CO)-R$$
$$HC-O-(CO)-R$$
$$(CH_2)_2-O-(CO)-R$$

where the R groups are derived from corn oil

3-Methyl-1,3,5-Pentane Triester

(16)
$$(CH_2)_2-O-(CO)-R$$
$$CH_3-C-O-(CO)-R$$
$$(CH_2)_2-O-(CO)-R$$

where the R groups are derived from high oleic sunflower oil

The triester compounds of this invention may be prepared using standard esterification techniques for triols (reviewed in Markley, K. S., *Fatty Acids*, 2nd ed., part 2, Krieger Pub. Co., 1983, pp. 785-787, 797-811, and 817-820). These include reactions of the fatty acids, acid chlorides or anhydrides with the triols, or transesterification between fatty acid esters (e.g., fatty acid methyl esters) and triols. For example, butanetriol triesters were synthesized by direct esterification in W. Ger. Pat. No. 850,610, and both butanetriol and hexanetriol triesters were synthesized in Nessner, R., 80 *Fette, Seifen, Anstrichm.* 303 and 461 (1978).

The dicarboxylate-extended fatty acid triester compounds of this invention may be prepared by reacting the fatty alcohols or fatty alcohol derivatives with the dicarboxylic acids, and then reacting the dicarboxylic acid-extended fatty alcohols with the triols.

EXAMPLES

The following examples are presented to further illustrate and explain the present invention and should not be taken as limiting in any regard. Unless otherwise indicated, all parts and percentages are by weight, and are based on the weight at the particular stage of the processing being described. The proton NMR spectra have assigned chemical shifts, multiplicities, and intensities consistent with the structures for which they are reported.

Example 1

This example describes the preparation of 1,2,6-hexane trioleate (also called 1,2,6-tris(oleoyloxy)hexane) a compound of this invention depicted in structure (3) above.

To a solution of 1,2,6-trihydroxyhexane (1.34 g, 0.01 mole) in 20 mL pyridine is added 10 mL (ca. 0.03 mole) oleoyl chloride. The mixture is shaken overnight and is filtered through silica, concentrated on the rotary evaporator, and refiltered to afford an oil.

Proton NMR spectrum in chloroform-d: chemical shift in ppm (multiplicity, intensity, assignment): 5.35 (multiplet, 6 H, HC=CH), 5.09 (multiplet, 1 H, methine), 3.90–4.26 (superimposed multiplets, 4 H, CH$_2$—O), 2.31 (superimposed triplets,triplets, 6 H, CH$_2$—CO$_2$), 2.01 (multiplet, 12 H, C=C—CH$_2$), 1.3-1.6 (multiplets, 66 H, CH$_2$) and 0.87 (triplet, 9 H, CH$_3$).

Example 2

In this example, 1,2,6-hexane tri-10-undecenoate, another triester of this invention (shown above as structure 12), is prepared.

To a solution of 1,2,6-trihydroxyhexane (1.34 g, 0.01 mole in 20 mL pyridine is added 6.5 mL 10-undecenoyl chloride. The mixture is shaken at ambient temperature overnight, filtered through silica, concentrated, and refiltered through silica to afford an oil.

Proton NMR spectrum in chloroform-d: chemical shift in ppm (multiplicity, intensity, assignment): 5.79 (multiplet, 3H, C=CH), 5.07 (multiplet, 1 H, methine proton), 4.93 (multiplet, 6 H, C=CH$_2$), 3.90–4.25 (superimposed multiplets, 4 H, CH$_2$—O), 2.30 (multiplet, 6 H, CH$_2$—CO$_2$), 2.01 (quartet, 6 H, C=C—CH$_2$) and 1.3-1.6 (multiplet, 42 H, CH$_2$).

Example 3

This example outlines the procedure for preparing 1,2,3-heptane tri-lo-undecenoate (illustrated above as structure 4).

To a solution of 1,2,3-heptanetriol (1.0 g, 0.007 mole) in 30 mL pyridine is added 5 mL 10-undecenoyl chloride and this mixture is shaken overnight at room temperature. Filtration through silica, concentration on the rotary evaporator, and re-filtration through silica affords an oil.

Proton NMR spectrum in chloroform-d: chemical shift in ppm (multiplicity, intensity, assignment): 5.80 (multiplet, 3 H, C=CH), 5.13 (multiplet, 1 H, methine proton), 4.95 (multiplet, 6 H, C=CH$_2$), 4.04–4.40 (multiplet, 3 H, methine H and CH$_2$—O), 2.31 (multiplet, 6 H, CH$_2$—CO$_2$), 2.02 (quartet, 6 H, C=C—CH$_2$), 1.60 (multiplet, 8 H, CH$_2$—C—O$_2$C and O$_2$C—C—CH$_2$), 1.31 (multiplet, 34 H, CH$_2$) and 0.87 (multiplet, 3 H, CH$_3$).

Example 4

1,2,4-Butane trioleate, a triester of this invention depicted above as structure 1, is prepared in this example.

Oleoyl chloride (255.78 g, 0.85 mole) is charged to a flask which contains a magnetic stirrer bar and which is cooled by means of an ice bath. A solution of 1,2,4-butanetriol (26.35 g, 0.25 mole) in 103 mL pyridine is added dropwise, giving rise to an exothermic reaction and concomitant production of a voluminous precipitate. After warming to ambient temperature and stirring for 24 hours the reaction mixture is diluted with twice its volume of hexane and the resulting solution passed through a silica column under flash chromatographic conditions. Evaporation of the hexane eluant followed by steam deodorization (15 g water, 200°, 0.6 Torr) of the residue affords 135 g (60%) of the title composition as a pale yellow oil.

Proton NMR spectrum in chloroform-d: chemical shift in ppm (multiplicity, intensity, assignment): 5.35 (multiplet, 6 H, HC=CH), 5.19 (quartet J=6.5 Hz of doublets J=3.25 Hz, 1 H, methine proton), 4.28 (doublet of doublets J=12.0 and 3.6 Hz, 1 H, one half of O—C—CH$_2$—O), 4.12 (overlapping triplets J=6.0 Hz, 2 H, O—CH$_2$—C—C—O), 4.06 (doublet of doublets J=12.0 and 6.0 Hz, 1 H, one half of P—C—CH$_2$—O), 2.79 (triplet, —0.6 H, C=C—CH$_2$—C=C, due to linoleic acid impurity in starting oleic acid), 2.30 (overlapping triplets, 6 H, O=C—CH$_2$), 2.02 (multiplet, 12 H, CH$_2$—C=C—CH$_2$), 1.93 (apparent quartet, 2 H, O—C—CH$_2$—C—O), 1.61 and 1.28 (multiplets, 60 H, —CH$_2$—) and 0.89 (triplet, 9 H, —CH$_3$).

FT-IR spectrum (neat): frequency in cm-1 (intensity): 2922.1 (s), 2852.7 (m), 1741.7 (s), 1464.0, 1240.2, 1165.0, 1116.0, 1089.5 and 723.3 (m).

Example 5

This example outlines a procedure for preparing 1,2,6-hexane trimyristate, a triester of this invention illustrated in structure (13) above.

To a solution of 1,2,6-trihydroxyhexane (1.34 g, 0.01 mole) in 20 mL pyridine is added 4.9 g (0.02 mole) myristoyl chloride. The mixture is shaken overnight at room temperature, filtered through silica, concentrated, and refiltered to afford the title compound as a solid.

Example 6

This example outlines preparation of another triester derivative of this invention, a 1,2,4-butane triester (depicted as structure (14) above).

A mixture of 3.3 g oleoyl chloride (0.011 mole), 2.7 g myristoyl chloride (0.011 mole) and 3.09 palmitoyl chloride (0.011 mole in 3o ml pyridine is shaken overnight with 1.3 g (0.011 mole) 1,2,4-butane triol. Filtration through silica, concentration and refiltration affords a functionally useful fat mimetic.

Example 7

This example outlines the procedure for screening the in vitro digestibility of the triester derivatives of this invention using pancreatic lipase.

Preparation of Reagents and Materials

1. Buffer: A pH 7.1 phosphate buffer is prepared by dissolving 6.8 g. KH$_2$PO$_4$ in 1 L. of millipore filtered water (to yield 0.05 M phosphate). Fifty mg. Ca(NO$_3$)$_2$ and 5.0 g. cholic acid (Na$^+$ salt, an ox bile isolate from Sigma) are added to give 0.3 mM Ca++ and 0.5% cholic acid in 0.05 M phosphate. The pH is adjusted to approximately 7.1 with solid NaOH. Several drops of Baker "Resi-analyzed " toluene are added to prevent bacterial growth during storage at 3°-5° C.

2. Lipase: About 15 mg/mL commercial porcine pancreatic lipase from U.S. Biochemical Corporation is dissolved in buffer.

3. Substrates and Standards: A 1.0 mL volumetric flask is charged with an amount of lipid substrate (test substance or standard) calculated to give a concentration of 200 nanomoles per microliter in Baker "Resi-analyzed " toluene. (The proper concentration may be approximated by doubling the molecular weight of the lipid in question, dividing by 10, and diluting to the mark; this yields about 200 nanomoles per microliter.) This preparation affords the substrate to be used in the hydrolysis reactions.

Fatty acids and glyceride standards from Nu Chek or Sigma are prepared for elution on TLC plates (prewashed with 1:1 chloroform/methanol) by diluting the substrate solution with 10:1 toluene (1 part substrate plus 9 parts toluene by volume) in septum vials.

Procedure

In a 25 mL Erlenmeyer, emulsify 20 mL buffer and 40 microliters of substrate using an ultrasonic disrupter at a microtip maximum setting for approximately 10 seconds. This results in a 0.4 microliter/milliliter emulsion. Place in a 37° C. water bath and stir vigorously. After temperature equilibration, add 40 microliters of enzyme solution and start timing. Remove 5.0 mL aliquots at convenient time intervals for analysis. To establish a standard curve for triolein, aliquots are taken at 10, 20, 30 and 40 minutes. A zero time control should be run for all test compounds.

Add the aliquot to a 15 mL glass centrifuge tube containing a drop of concentrated HCl. Add approximately 3 mL of a 2:1 mixture of $CHCl_3:CH_3OH$ and shake vigorously. Centrifuge at approximately 5000 rpm for 5 minutes and transfer the bottom layer with a Pasteur pipet to a 5 mL septum vial. Repeat the extraction step once and combine the two bottom layers. Evaporate the solvent in nitrogen gas. After about half of the solvent is removed, add an equivalent volume absolute ethanol and continue evaporation in a nitrogen stream until dryness is achieved. Samples may be warmed with a heat gun to facilitate drying.

When the samples are dry, add exactly 200 microliters of toluene containing 10% DMSO, cap tightly, and spot TLC plate with 2.0 microliters per channel. (If 100% extraction efficiency of a zero time control is achieved, this amounts to 20 nanomoles of substrate spotted on the plate.) Develop with a suitable solvent system, for example, hexane: ethyl ether: acetic acid in a volume ratio of 60:40:1. After 15 cm elution, dry plate with a heat gun and determine amounts of starting substrate and products of hydrolysis by scanning 10 to 20 nanomoles per channel at a wavelength of 190 nm using the CAMAG TLC Scanner II densitometer equipped with a Spectra Physics 4270 integrator and comparing with controls run at the same time.

Results

Using this procedure and enzyme system, a triglyceride control, triolein, is hydrolyzed about 90% in two hours. Using the same procedure, enzyme system, and two-hour incubation, butane trioleate prepared in Example 4 is hydrolyzed approximately 50%.

Example 8

This example describes another lipase assay employing the same procedure and enzyme system as that described in Example 7 above, except that super fluid chromatography instead of thin layer chromatography is employed to separate the products of hydrolysis. After incubation for one hour with pancreatic lipase, a triglyceride control, trimyristin, is almost fully hydrolyzed. Using the same procedure, enzyme system, and incubation period, hexane trimyristate prepared in Example 5 is hydrolyzed approximately 20%.

Example 9

This example illustrates how the triol triesters of this invention are screened for caloric availability by a carefully controlled in vivo animal feeding study.

An experimental relationship between total calories ingested and animal body weight gain is established by monitoring the body weight gain associated with consumption of a nutritionally balanced diet containing varying concentrations of a reference substance such as corn oil which has a known caloric availability. Correlations between total calories ingested and body weight gain are excellent (r=0.99).

Caloric availability of an unknown substance is evaluated by substituting a specific weight of the unknown substance for the reference substance and observing the body weight gain. The gain in body weight is equated to a total number of calories using the correlation previously established for the reference data. The estimated number of calories ingested are divided by the weight of unknown substance to give the apparent calories per gram for the unknown substance. Generally speaking, in these bioavailability studies, the degree of perianal pelt soiling correlates with reduced bioavailability.

The test animals are six-week-old male Sprague-Dawley rats obtained from the Portage, Michigan facility of the Charles River Laboratories, Inc. After acclimation for 15 days, the test duration is 14 days. The dietary requirements are established by observing the actual feed consumption of animals provided with unlimited feed. All diets are prepared to contain 50% of the established dietary requirements plus any supplements of reference or unknown substances. In all tests so designed the test animals are maintained in very good health.

The test feeds are AIN-76A and fortified AIN-76 (hereinafter abbreviated "fort") AIN-76A (Teklad). The major components of these diets are as follows:

| component | AIN-76A | fortified AIN-76A |
|---|---|---|
| casein | 20% | 40% |
| corn starch | 15 | 8.08 |
| sucrose | 50 | 26.02 |
| fiber | 5 | 5 |
| corn oil | 5 | 5 |
| AIN mineral mix | 3.5 | 7 |
| AIN vitamin mix | 1 | 2 |
| choline | 0.2 | 0.4 |
| methionine | 0.3 | 0.6 |
| total | 100% | 100% |
| calc. caloric density | 3.85 kcal/gm | 3.9 kcal/gm |

Using these diets supplemented by reference or unknown substances fed as microencapsulated oils, sample body weight (hereinafter abbreviated "wgt") gains for example animals A and B fed corn oil as a reference (9.0 calories/gram) are as follows:

| | Animal A | | Animal B | |
|---|---|---|---|---|
| diet supplied | wgt gain (grams) | calories consumed | wgt gain (grams) | calories consumed |
| ad lib AIN-76A | 73.6 | 1275 | 82.4 | 1370 |
| 50% fort | −3.4 | 651 | −3.8 | 691 |
| 50% fort + 7.75% gelatin | 9.0 | 705 | 8.3 | 747 |
| 50% fort + 7% corn oil | 13.9 | 768 | 15.2 | 831 |
| 50% fort + 14% corn oil | 28.3 | 913 | 37.9 | 998 |
| 50% fort + 21% corn oil | 57.7 | 1093 | 63.3 | 1183 |

Rats were fed a diet of 50% fort and 21% 1,2,4-butane tioleate prepared in Example 4 as a test compound under the foregoing procedure, and their weight gain was determined. Based upon the base line control data, and the data from the test compound, it was determined that 1,2,4-butane trioleate yielded about 7.7 kcal/gram upon being metabolized.

Example 10

Sweet Chocolate. A low calorie sweet chocolate may be prepared by blending

| Ingredient | parts |
|---|---|
| Cocoa Powder | 1.0 |
| Sugar | 1.0 |

To this is added a portion of

| | |
|---|---|
| Example 5 Triester | 1.0 |

Mix thoroughly and pass through a refiner to reduce the particles to desired size. The material is conched, and the remaining fat mimetic is added. The mixture is poured into molds and quenched cooled. No tempering regimen is necessary.

Chocolate Chips. The chocolate prepared above is deposited into nibs and processed in the usual process.

Example 11

Chewy Chocolate Chip Cookies. Chewy chocolate chip cookies may be prepared by combining

| Ingredient | parts |
|---|---|
| Sugar | 24.3 |
| Invert Sugar | 20.0 |
| Flour | 13.7 |
| Example 2 Triester | 13.0 |
| Frozen Whole Eggs | 2.0 |
| Sodium Bicarbonate | 0.1 |
| Monocalcium Phosphate | 0.1 |
| Vanillin | 0.1 |
| Water | 7.7 |

To this is added

| | |
|---|---|
| Example 10 Chocolate Chips | 19.0 | and mixed until just dispersed prior to depositing and baking in the usual process.

Example 12

Sandwich Cookies. A basecake may be prepared by combining

| Ingredient | parts |
|---|---|
| Flour | 48.0 |
| High Fructose Corn Syrup | 12.0 |
| Sugar (6X) | 10.0 |
| Example 3 Triester | 10.0 |
| Dutched Cocoa | 5.0 |
| Corn Syrup (42 D.E.) | 3.0 |
| Dextrose | 2.0 |
| Frozen Whole Eggs | 2.0 |
| Salt | 0.3 |
| Sodium Bicarbonate | 0.2 |
| Lecithin | 0.2 |
| Vanilla | 0.2 |
| Ammonium Bicarbonate | 0.1 |
| Water | 7.0 | mixing well, rotary molding, baking and cooling. A filler may be prepared by melting

| | |
|---|---|
| Example 5 Triester | 37.0 | and adding

| | |
|---|---|
| Sugar 10X | 62.7 |
| Vanillin | 0.3 |

Cool filler to 78° F. and sandwich between base cakes in a ratio of 1 to 3.

Example 13

Chocolate Icing. Chocolate icing may be prepared by blending, being careful not to incorporate air

| Ingredient | parts |
|---|---|
| Sugar (12X) | 65.0 |
| Example 6 Triester | 11.0 |
| Dutched cocoa | 10.5 |
| Nonfat Dry Milk | 4.0 |
| Frozen Egg Yolk | 4.0 |
| Salt | 0.25 |
| Vanilla | 0.25 |
| Water | 5.0 |

The icing can be prepared by combining

| Ingredient | parts |
|---|---|
| Nonfat Milk | 96.4 |
| Example 1 Triester | 3.5 |
| Lecithin | 0.1 | mixing and homogenizing.

| Ingredient | parts |
|---|---|
| Example 3 Triester | 26.0 |
| with Mono- and Di-glycerides | 2.0. |

An aqueous phase is prepared by dissolving

| | |
|---|---|
| Water | 46.6 |
| Sugar (4X) | 23.0 |
| Dextrose | 1.0 |
| Polysorbate 60 | 0.7 |
| Sorbitan Monostearate | 0.3 |
| Carageenan | 0.2 |
| Guar Gum | 0.1 |
| Vanilla | 0.1. |

The oil blend is then added to the aqueous phase with high agitation. The topping can be packaged and refrigerated or frozen.

Example 15

Peanut Butter. Peanut butter may be prepared by mixing

| Ingredient | parts |
|---|---|
| Example 6 Triester | 35.0 |
| with Peanut Flavor | 2.0. |
| Then Corn Syrup Solids | 12.0 |
| Salt | 1.0 |
| High Fructose Corn Syrup | 10.0 | are added while agitating. When well blended, add

| | |
|---|---|
| Defatted Peanut Flour | 40.0 | mix and package.

Example 16

Sprayed Crackers. A dough prepared from

| Ingredient | parts |
|---|---|
| Flour | 100 |
| Sugar | 5.0 |
| Malt | 1.5 |
| Example 4 Triester | 7.5 |
| Salt | 1.0 |
| Sodium Bicarbonate | 0.9 |
| Nonfat Dry Milk | 2.5 |
| High Fructose Corn Syrup | 2.5 |
| Monocalcium Phosphate | 0.75 |
| Water | 28 | is sheeted, stamped, and baked to produce a cracker product, then sprayed with Example 4 triester prior to packaging.

Example 17

Ice Cream. Vanilla ice cream may be prepared by mixing

| Ingredient | parts |
|---|---|
| Sugar (10×) | 15.0 |
| Nonfat Dry Milk | 3.9 |
| Salt | 0.4 |
| into Water | 39.0 | for 3 minutes. Then add melted

| Example 5 Triester | 28.4 |
|---|---| and cook to 200° F. while mixing. Hold for 1 minute. Cool to 160°60 F., and add

| Sugared Egg Yolks | 12.5 |
|---|---|
| Vanilla Extract | 0.8 | and mix 1 minute. Cool and freeze to desired overrun.

Example 18

Low Calorie Milk. A low calorie "whole milk" may be prepared by combining

| Ingredient | parts |
|---|---|
| Nonfat Milk | 96.4 |
| Example 1 Triester | 3.5 |
| Lecithin | 0.1 | mixing and homogenizing.

Example 19

Cream Cheese. To make an imitation cream cheese, add

| Ingredient | parts |
|---|---|
| Water | 53 |
| to Calcium Caseinate | 6.7 |
| Buttermilk Powder | 3.9 |
| Emulsifiers | 0.2 |
| Xanthan Gum | 0.2 | and mix three minutes. Melt

| Example 5 Triester | 35.5 |
|---|---| and cook to 200° F. while mixing. Hold for one minute. Then cool to 150° F. and add

| Flavor, Acid and Color | 0.5 |
|---|---| and mix one minute. Fill, then cool and store.

Example 20

Cheddar-Style Cheese. To make Cheddar-style cheese, homogenize

| Ingredient | parts |
|---|---|
| Nonfat Milk | 75.0 |
| Low Temperature Nonfat Dry Milk | 4.0 |
| Example 2 Triester | 20.0 |

To this is added

| Salt | 0.7 |
|---|---|
| Lactic Acid Culture | 0.3 |

The mixture is fermented and pressed to a final composition of approximately 37.0% moisture, 63.0% total solids, and 32.0% triester.

Example 21

Imitation Sour Cream. An imitation sour cream may be prepared by adding

| Ingredient | parts |
|---|---|
| Water | 75.8 |
| to Modified Starch | 2.0 |
| Avicel | 1.0 |
| Distilled Monoglyceride | 0.7 |
| and Polysorbate 60 | 0.3 | and mixing three minutes. To this is added

| Example 1 Triester | 16.5 |
|---|---|
| Condensed Skim Milk | 3.5 | and the mixture mixed three minutes, cooked to 195° F., and held five minutes. This may then be cooled to 60° F., and

| Flavors and Acids | 0.2 |
|---|---| added, followed by filling in the usual process.

Example 22

Salad Dressing. Salad dressing may be prepared by adding

| Ingredient | parts |
|---|---|
| Water | 29.0 |
| to Sugar | 12.0 |

-continued

| Ingredient | parts |
|---|---|
| and Spices | 4.5 | and mixing three minutes. Then

| Salted Egg Yolks | 5.5 |
|---|---|
| and Modified Starch | 3.0 | are added and mixed two minutes. To the aqueous mixture are added

| Example 4 Triester | 20.0 |
|---|---|
| and Corn Oil | 20.0 |
| then 120 Distilled Vinegar | 6.0 |

The mixture is then mixed three minutes and passed through a colloid mill set at 60 prior to filling in the usual process.

Example 23

Margarine. A margarine may be prepared by emulsifying

| | parts |
|---|---|
| Oil Phase Ingredients | |
| Example 6 Triester | 68.6 |
| Liquid Corn Oil | 0.55 |
| Partially Hydrogenated Corn Oil | 0.45 |
| Lecithin | 0.30 |
| Mono- and Di-Glycerides | 0.21 |
| Margarine Flavor and Color | 0.0062 |
| Aqueous Phase Ingredients | |
| Water | 25.8 |
| Whey | 1.00 |
| Salt | 2.00 |
| Sodium Benzoate | 0.086 |
| Potassium sorbate | 0.066 |
| Calcium EDTA | 0.0015 | and passing the emulsion through a cool scraped surface heat exchanger in the usual process.

Example 24

Shortening. A shortening may be prepared by mixing

| Ingredient | parts |
|---|---|
| Example 6 Triester | 95 |
| with Soybean Oil (70 IV) | 5 |
| Mono- and Diglycerides | |

Example 25

Frying Oil. A frying oil may be prepared by adding 1 ppm polydimethylsiloxane to Example 2 Triester.

Example 26

Potato Chips. Whole peeled potatoes may be sliced, washed in water, and fried in a 1:1 mixture of Example 3 Triester and peanut oil at 375° F. to desired color. The excess oil is shaken off and the chips are salted. The finished product contains about 35% fat and fat mimetic.

Example 27

Bologna. To make bologna, chop together

| Ingredient | parts |
|---|---|
| Boneless Mutton | 40.0 |
| Pork Hearts | 15.0 |
| Beef Trimmings (75/25) | 10.0 |
| Pork Blade Meat | 5.0 |
| adding ice to control temperature. Then add | |
| Seasoning | 7.0 |
| Example 1 Triester | 13.0 |
| and Water/Ice | 10.0 |

The mixture can be stuffed into casing, smoked, and packaged.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. An edible composition comprising edible ingredients and a fat mimetic compound of the following formula

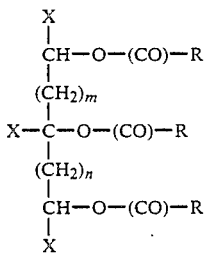

where
m = 0 to 20,
n = 0 to 20,
X = H or an aliphatic having 1 to 20 carbons, the X groups being the same or different, and
each R is, independently, a $C_2$ to $C_{29}$ ester group of the formula

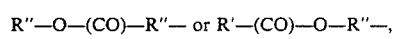

where R'— and R"— are, independently, aliphatic groups, subject to the proviso that, when X=H, then m+n≧1 and to the proviso that the number of carbons in the X groups, together with the sum of m+n, does not exceed 25.

2. A composition according to claim 1 wherein the X group attached to the carbon bearing the central ester group is an aliphatic group.

3. An edible composition comprising edible ingredients and a fat mimetic compound of the following formula:

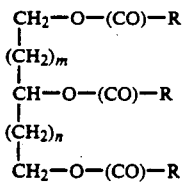

where
m = 1 to 14,
n = 0 to 14,
provided that $m+n \leq 26$, and
each R is, independently, a $C_2$ to $C_{29}$ ester group of the formula

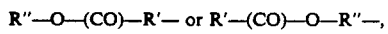

where R'— R"— are, independently, aliphatic groups.

4. An edible composition comprising edible ingredients and a fat mimetic compound of the following formula:

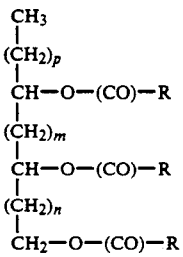

where
m = 0 to 13,
n = 0 to 13,
p = 0 to 13,
provided that $m+n+p \leq 26$, and
each R is, independently, a $C_2$ to $C_{29}$ ester group of the formula

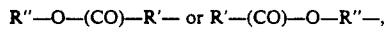

where R'— and R"— are, independently, aliphatic groups.

5. The composition according to claims 1 to 4 wherein the R groups comprise ester groups of the formula R"—O—(CO)—R'—.

6. A composition according to claims 1 to 4 wherein the R groups are derived from fatty acids selected from the group consisting of acetic, propionic, butyric, caproic, caprylic, pelargonic, capric, undecanoic, lauric, myristic, palmitic, margaric, stearic, arachidic, behenic, lignoceric, cerotic, montanic, melissic, palmitoleic, oleic, vaccenic, linoleic, linolenic, eleostearic, arachidonic, nervonic, eicosapentaenoic, docosatetraenoic, docosapentaenoic, and docosahexaenoic acids, and mixtures thereof.

7. A composition according to claims 1 to 4 wherein the R groups are derived from non-hydrogenated, partially hydrogenated or fully hydrogenated oils selected from the group consisting of soybean, safflower, sunflower, sesame, peanut, corn, olive, rice bran, canola, babassu nut, coconut, palm, palm kernel, lupin, nasturtium seed, mustard seed, cottonseed, low erucic rapeseed, butter and marine oils, and fractions thereof.

8. A composition according to claim 1 to 4 wherein said edible composition is a food composition selected from the group consisting of dairy products, bakery products, meat products, fatty candies, margarines, and frying oils.

9. A composition according to claim 8 wherein said bakery products are cookies or crackers.

10. A composition according to claim 8 wherein said dairy product is selected from the group consisting of ice cream, margarine, and filled cream.

11. A composition according to claim 8 wherein said dairy products are cheese.

12. A method for reducing the available calories in a food composition having an edible fat component, which method consists of replacing at least a substantial portion of the edible fat with a compound of the formula

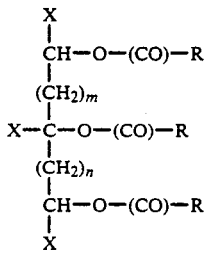

where
m = 0 to 20,
n = 0 to 20,
X = H or an aliphatic having 1 to 20 carbons, the X groups being the same or different, and
each R is, independently, a $C_2$ to $C_{29}$ ester group of the formula

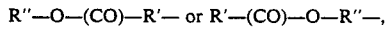

where R'— and R"— are, independently, aliphatic groups, subject to the proviso that, when X=H, then $m+n \geq 1$ and to the proviso that the number of carbons in the X groups, together with the sum of m+n, does not exceed 25.

13. A method according to claim 12 wherein said compound provides 0.5 to 8.5 kcal/gram.

14. A method according to claim 13 wherein said compound provides 2.0 to 6.0 kcal/gram.

15. A method according to claim 14 wherein said compound provides 1.0 to 6.0 kcal/gram.

16. A method according to claim 14 wherein said food composition is selected from the group consisting of margarine, mayonnaise, mustard, frying fat, meat products, fatty candy, chewing gum, and bakery products.

17. A method of preparing a reduced calorie food composition which comprises formulating said composition with a composition as defined in any of claim 1 to 4.

18. A composition according to claim 5 wherein said ester group is a dicarboxylate-extended fatty group selected from the group consisting of malonyl-, succinyl-, glutaryl- and adipoyl-extended fatty alcohols.

19. A composition according to claims 1 to 4 wherein said ester group has the formula R'—(CO)—O—R"—.

20. A composition according to claim 19 wherein said ester group is an hydroxycarboxylic acid-extended fatty acid.

21. In a fat-containing food composition, an improvement wherein at least a portion of said fat is replaced by a fat mimetic compound comprising a $C_4$ to $C_{30}$ aliphatic triol esterified with $C_2$ to $C_{29}$ dicarboxylate-extended fatty alcohol groups.

22. In a fat-containing food composition, an improvement wherein at least a portion of said fat is replaced by a fat mimetic compound comprising a $C_4$ to $C_{30}$ aliphatic triol esterified with $C_2$ to $C_{29}$ hydroxycarboxylic-extended fatty acid groups.

23. An improvement according to claim 21 or 22 wherein said extended groups have 3 to 23 carbons.

* * * * *